United States Patent [19]

Zizek et al.

[11] Patent Number: 4,720,552
[45] Date of Patent: Jan. 19, 1988

[54] PROCESS FOR THE PREPARATION OF ACID ADDITION SALTS OF 4(5)-METHYL-5(4)-THIOMETHYL IMIDAZOLE

[75] Inventors: Teofil Zizek; Janko Zmitek, both of Ljubljana, Yugoslavia

[73] Assignee: LEK, tovarna facmacevtskih in kemicnih izdelkov, n.sol.o, Ljubljana, Yugoslavia

[21] Appl. No.: 43,125

[22] Filed: Apr. 27, 1987

[30] Foreign Application Priority Data

May 8, 1986 [YU] Yugoslavia ............................ 745/86

[51] Int. Cl.$^4$ .......................................... C07D 233/64
[52] U.S. Cl. ................................................. 548/342
[58] Field of Search ........................................ 548/342

[56] References Cited

PUBLICATIONS

*Chemical Abstracts,* 91:175352 (1979) [Ger. Offen. 2,855,836, Baudet, et al., 7/12/79].

*Primary Examiner*—Richard A. Schwartz
*Attorney, Agent, or Firm*—Pollock, Vande Sande & Priddy

[57] ABSTRACT

A new, technologically easily feasible process for the preparation of 4(5)-methyl-5(4)-thiomethyl imidazole of the formula

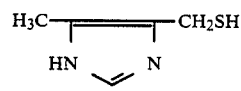

and of acid addition salts thereof is described, wherein 4(5)-methyl-5(4)-bromomethyl imidazole hydrobromide is reacted in an aqueous medium at room temperature with potassium O-ethyl dithiocarbonate to the intermediate O-ethyl-S-(4-methylimidazolyl-5-methyl) dithiocarbonate, which is hydrolyzed at the reflux temperature under nitrogen atmosphere with an aqueous HBr or HCl solution to 4(5)-methyl-5(4)-thiomethyl imidazole hydrobromide or hydrochloride resp.

The compound is a valuable starting material in the synthesis of cimetidine, a well-known drug in the therapy of the ulcer disease.

2 Claims, No Drawings

PROCESS FOR THE PREPARATION OF ACID ADDITION SALTS OF 4(5)-METHYL-5(4)-THIOMETHYL IMIDAZOLE

TECHNICAL FIELD OF THE INVENTION (IPC C 07 D 233/64)

The present invention relates to a new process for the preparation of 4(5)-methyl-5(4)-thiomethyl imidazole of the formula

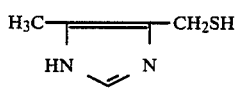

and of acid addition salts thereof.

The above compound in the form of its hydrochloride or hydrobromide salt is a valuable starting material in the synthesis of cimetidine, a well-known drug in the therapy of the ulcer disease.

TECHNICAL PROBLEM

There is a constant need of a technologically advantageous process for the preparation of 4(5)-methyl-5(4)-thiomethyl imidazole in the form of its hydrochloride or hydrobromide salt, which would afford the desired compound in good yield, with high purity and in a swift way.

PRIOR ART

4(5)-methyl-5(4)-thiomethyl imidazole and its hydrochloride salt are known compounds that are disclosed in DE-OS 28 55 836 as a starting compound in the synthesis of cimetidine.

The process of the synthesis of 4(5)-methyl-5(4)-thiomethyl imidazole and its hydrochloride salt as described therein is carried out in a known way for the synthesis of thiols as described in literature (J. L. Wardell in: The Chemistry of the Thiol Group, S. Patai, Ed. Interscience, New York 1974, Ch. 4 in reference).

The starting 4(5)-methyl-5(4)-chloromethyl imidazole hydrochloride is reacted with potassium O-ethyl dithiocarbonate (potassium ethyl xanthate) in an ethanolic solution at the reflux temperature of the reaction mixture to the intermediate O-ethyl-S-(4-methyl-imidazolyl-5-methyl)dithiocarbonate /4-methyl-5-(ethoxydithioformyl)imidazole/, which is isolated and then hydrolyzed with HCl at the reflux temperature of the reaction mixture to 4(5)-methyl-5(4)thiomethyl imidazole hydrochloride in a yield of 70%.

DESCRIPTION OF THE SOLUTION OF THE TECHNICAL PROBLEM WITH EXAMPLES

According to the process of the invention 4(5)-methyl-5(4)-bromomethyl imidazole hydrobromide, which is a known compound described in literature (H. G. Lennartz, W. Schunack, Arch. Pharm. (Weinhein) 310, 1019–1022, 1977; P. Kairisalo, E. Honkanen, Arch. Pharm. (Weinhein) 316, 688–690, 1983; R. Tozo et al, Gazz. Chim. Ital 109, 529–533, 1979), is reacted with potassium O-ethyl dithiocarbonate in an aqueous medium at room temperature to the intermediate O-ethyl-S-(4-methyl-imidazolyl-5-methyl)dithiocarbonate, which is, without isolation, immediately hydrolyzed in the presence of a diluted aqueous solution of HBr or HCl to 4(5)-methyl-5(4)-thiomethyl imidazole in the form of its hydrobromide or hydrochloride salt. The yield of the synthesis is 85%.

The reaction is carried out in nitrogen atmosphere in order to prevent the formation of disulfide as a result of the oxidation of the desired thiol.

When compared to the process for the synthesis of the title compound in accordance with DE-OS 28 55 836, the present process is distinguished by the single stage procedure without the isolation of the intermediate dithiocarbonate; in addition, the reaction of 4(5)-methyl-5(4)-bromomethyl imidazole hydrochloride with potassium O-ethyl dithiocarbonate in an aqueous medium at room temperature is practically instantaneous. The present process affords better yields of the title compound within shorter times.

Reaction scheme:

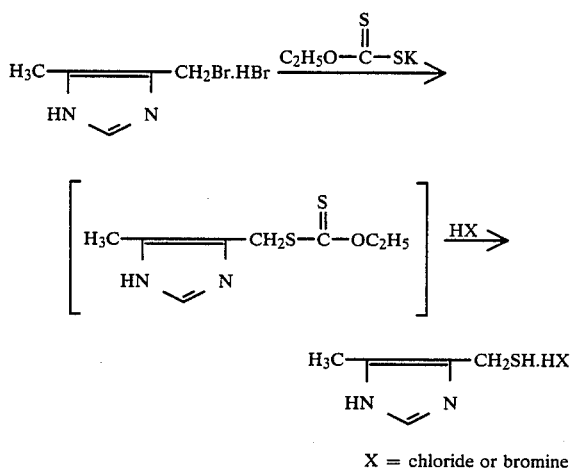

X = chloride or bromine

EXAMPLE 1

To a solution of potassium O-ethyl dithiocarbonate (1.9 g, 0.012 moles) in water (5 ml) there is added, under vigorous stirring and under nitrogen atmosphere at room temperature, 4(5)-methyl-5(4)-bromomethyl imidazole hydrobromide (3 g, 0.012 moles). To the dense crystalline precipitate of the intermediate O-ethyl-S-(4-methyl-imidazolyl-5-methyl)dithiocarbonate which separates, there is added an aqueous HBr solution (48%; 12 ml). The reaction mixture is heated to the reflux temperature and refluxed for two more hours. The reaction mixture is concentrated by evaporation under reduced temperature, cooled and the resulting precipitate is sucked off. Thus there are obtained 2.08 g (85%) of 4(5)-methyl-5(4)-thiomethyl imidazole hydrobromide, m.p. 193°–198° C.

EXAMPLE 2

The procedure of the Example 1 is repeated except that the hydrolysis of the intermediate compound is effected in the presence of an aqueous HCl solution (36%; 12 ml). Thus there are obtained 1.64 g (85%) of 4(5)-methyl-5(4)-thiomethyl imidazole hydrochloride, m.p. 225°–227° C.

We claim:

1. A process for the preparation of a hydrogenhalide acid addition salt of 4(5)-methyl-5(4)-thiomethyl imidazole of the formula

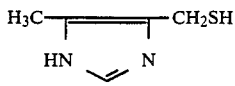

characterized in that 4(5)-methyl-5(4)-bromomethyl imidazole hydrobromide is reacted with potassium O-ethyl dithiocarbonate in an aqueous medium at room temperature to O-ethyl-S-(4-methyl-imidazolyl-5-methyl)dithiocarbonate, which is, without isolation, immediately hydrolyzed under nitrogen atmosphere with an aqueous solution of a hydrohalic acid at the reflux temperature of the reaction mixture to 4(5)-methyl-5(4)-thiomethyl imidazole hydrogenhalide.

2. A process according to claim 1, characterized in that the hydrolysis is carried out in the presence of a diluted aqueous HBr or HCl solution.

* * * * *